(12) United States Patent
Lang et al.

(10) Patent No.: US 6,626,962 B1
(45) Date of Patent: Sep. 30, 2003

(54) MIXTURE FOR THE OXIDATION TINTING OF KERATIN FIBERS CONTAINING A LACCASE AND TINTING METHOD USING SAID MIXTURE

(75) Inventors: Gérard Lang, Saint Prix (FR); Jean Cotteret, Verneuil sur Seine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/600,106

(22) PCT Filed: Jan. 12, 1999

(86) PCT No.: PCT/FR99/00036

§ 371 (c)(1),
(2), (4) Date: Sep. 5, 2000

(87) PCT Pub. No.: WO99/36043

PCT Pub. Date: Jul. 22, 1999

(30) Foreign Application Priority Data

Jan. 13, 1998 (FR) .......................................... 98 00251

(51) Int. Cl.⁷ ................................................. A61K 7/13
(52) U.S. Cl. ..................... 8/405; 8/406; 8/516; 424/62
(58) Field of Search .......................... 8/406, 405, 10.2, 8/516; 424/62

(56) References Cited

U.S. PATENT DOCUMENTS

| | | | |
|---|---|---|---|
| 3,251,742 A | 5/1966 | Soloway ...................... | 167/88 |
| 3,907,799 A | 9/1975 | O'Brien et al. ............. | 260/256 |
| 4,003,699 A | 1/1977 | Rose et al. .................... | 8/10.2 |
| 4,823,985 A | 4/1989 | Grollier et al. ................ | 922/1 |
| 5,061,289 A | 10/1991 | Clausen et al. ................ | 8/405 |
| 5,254,335 A | * 10/1993 | Deppert et al. ............... | 424/70 |
| 5,380,340 A | 1/1995 | Neunhoeffer et al. .......... | 8/406 |
| 5,766,576 A | 6/1998 | Löwe et al. ................... | 424/62 |
| 5,935,560 A | * 8/1999 | Seper et al. ............. | 424/10.12 |
| 6,132,707 A | * 10/2000 | Dubief et al. ............ | 424/70.08 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 181 773 | 5/1986 |
| EP | 0 227 994 | 7/1987 |
| EP | 0 473 508 | 3/1992 |
| EP | 0 486 135 | 5/1992 |
| EP | 0 504 005 | 9/1992 |
| EP | 0 628 559 | 12/1994 |
| EP | 0 692 244 | 1/1996 |
| FR | 2 112 549 | 6/1972 |
| FR | 2 586 913 | 3/1987 |
| FR | 2 694 018 | 1/1994 |
| FR | 2 733 749 | 11/1996 |
| FR | 2 740 035 | 4/1997 |
| GB | 1 026 978 | 4/1966 |
| GB | 1 153 196 | 5/1969 |
| JP | 2-19576 | 1/1990 |
| JP | 5-163124 | 6/1993 |
| WO | WO 92/05764 | 4/1992 |
| WO | WO 93/05762 | 4/1993 |
| WO | WO 93/11103 | 6/1993 |
| WO | WO 94/07844 | 4/1994 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/15765 | 5/1996 |
| WO | WO 97/19998 | 6/1997 |
| WO | WO-9719998 | * 6/1997 |
| WO | WO 97/19999 | 6/1997 |

OTHER PUBLICATIONS

Vishnu J. Ram et al., "Synthesis of bioisosteric pyrazolo[1–5–α]pyrimidines as leishmanicides", Indian Journal of Chemistry, vol. 34B, Jun. 1995, pp. 514–520.

Robert H. Springer et al., "Synthesis and Enzymic Activity of 6–Carbethoxy– and 6–Ethoxy–3,7–disubstituted–pyrazolo[1,5–α]pyrimidines and Related Derivatives as Adenosine Cyclic 3',5'–Phosphate Phosphodiesterase Inhibitors", J. Med. Chem., vol. 25, 1982, pp. 235–242.

Thomas Novinson et al., "Synthesis and Antifungal Properties of Certain 7–Alkylaminopyrazolo[1,5–α]pyrimidines", J. Med. Chem. vol. 20, No. 2, 1977, pp. 296–299.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine With β–Aminocrotononitrile: Synthesis of 2,7–Dimethyl–5–Aminopyrazolo[1,5–α]pyrimidine", Heterocycles, vol. 6, Nos. 9,10, 1977, pp. 1355–1360.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

Ermitas Alcalde, "Etude de la réaction du β–aminocrotonitrile et du α–formly phénylacétonitrile avec l'hydrazine: synthèse d'amino–7 pyrazolo[1,5–α]pyrimidines", Journal of Heterocylic Chemistry, vol. 11, No. 3, Jun. 1974, pp. 423–429.

(List continued on next page.)

Primary Examiner—Gregory Delcotto
Assistant Examiner—Eisa Elhilo
(74) Attorney, Agent, or Firm—Finnegan, Henderson, Farabow, Garrett & Dunner, LLP

(57) ABSTRACT

The invention relates to a cosmetic mixture for the oxidation tinting of keratin fibers, especially human hair, comprising in a support material suitable for tinting keratin fibers (a) at least one laccase-type enzyme; (b) at least one particular conditioning agent for keratin fibers which is insoluble in aqueous media; and (c) at least one oxidation colorant. The invention also relates to the tinting methods using the above mixture.

44 Claims, No Drawings

OTHER PUBLICATIONS

Kirk–Othmer, "Surfactants and Detersive Systems", Encyclopedia of Chemical Technology, Third Edition, vol. 22, 1978, pp. 332–432.

Philip W. Wertz, PhD. et al., "Essential Fatty Acids and Epidermal Integrity", Arch. Dermatol., vol. 123, No. 10, Oct. 1987, pp. 1381–1384.

English language Derwent Abstract of EP 0 473 508. Mar. 4, 1992.

English language Derwent Abstract of EP 0 504 005. Sep. 16, 1992.

English language Derwent Abstract of EP 0 692 244. Jan. 1996.

English language Derwent Abstract of FR 2 112 549. No dates.

English language Derwent Abstract of FR 2 694 018. Jan. 1994.

English language Derwent Abstract of FR 2 740 035. Apr. 1997.

English language Derwent Abstract of FR 2 733 749. Nov. 1996.

English language Derwent Abstract of JP 2–19576. Jan. 1990.

English language Derwent Abstract of JP 5–163124. Jun. 1993.

\* cited by examiner

MIXTURE FOR THE OXIDATION TINTING OF KERATIN FIBERS CONTAINING A LACCASE AND TINTING METHOD USING SAID MIXTURE

The present invention relates to a composition for the oxidation dyeing of keratinous fibres comprising at least one enzyme of the laccase type, at least one oxidation dye and at least one particular keratinous fibre conditioning agent which is insoluble in aqueous media, as well as its uses for dyeing keratinous fibres, in particular human hair.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in U.S. Pat. No. 3,251,742, Patent Applications FR-A-2,112,549, FR-A-2,694,018, EP-A-0, 504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The Applicant has surprisingly discovered novel compositions comprising, as oxidizing system, at least one enzyme of the laccase type and at least one particular conditioning agent insoluble in aqueous media which will be defined in greater detail below, capable of constituting, in the presence of at least one oxidation dye, ready-to-use dyeing formulations giving colours which are more homogeneous, more intense and more chromatic without causing significant degradation or decolouring of the keratinous fibres, which exhibit low selectivity and good resistance to various attacks to which the hair may be subjected.

These discoveries form the basis of the present invention.

The first subject of the present invention is therefore a ready-to-use composition intended for the oxidation dyeing of keratinous fibres, in particular human keratinous fibres and more particularly human hair, comprising, in a carrier appropriate for keratinous fibres:

(a) at least one enzyme of the laccase type;
(b) at least one conditioning agent insoluble in aqueous media, chosen from the group consisting of: poly-α-olefins, fluorinated oils, vegetable oils, natural waxes, fluorinated waxes, fluorinated gums, fatty acid esters chosen from ethyl and isopropyl palmitates, 2-ethylhexyl palmitate, 2-octyldecyl palmitate, butyl, cetyl or 2-octyldodecyl myristates, hexyl stearate, butyl stearate, dioctyl maleate, hexyl laurate, 2-hexyldecyl laurate and isononyl isononanate, insoluble silicones, amide compounds comprising at least one fatty chain chosen from those of the following formula (1):

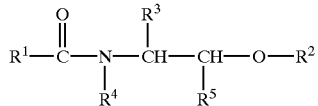

$$(1)$$

in which:

$R^1$ denotes either a saturated or unsaturated, linear or branched, $C_9$–$C_{30}$ hydrocarbon radical, it being possible for this radical to be substituted with one or more hydroxyl groups optionally esterified with a saturated or unsaturated $C_{16}$–$C_{30}$ fatty acid; or a radical R''—(NR—CO)$_n$—R' in which n is equal to 0 or 1, R denotes hydrogen or hydroxyethyl, R' and R'' are hydrocarbon radicals in which the sum of the carbon atoms is between 9 and 30, R' being a divalent radical, $R^2$ denotes a hydrogen atom or a (glycosyl)$_n$, (galactosyl)$_m$ or sulphogalactosyl radical in which n is an integer varying from 1 to 4 and m is an integer varying from 1 to 8;

$R^3$ denotes a hydrogen atom or a saturated or unsaturated $C_{16}$–$C_{27}$ hydrocarbon radical, it being possible for this radical to be substituted with one or more $C_1$–$C_{14}$ alkyl radicals; $R^3$ may also denote a $C_{15}$–$C_{26}$ α-hydroxyalkyl radical, the hydroxyl group being optionally esterified with a $C_{16}$–$C_{30}$ α-hydroxy acid;

$R^4$ denotes a hydrogen atom, a saturated or unsaturated $C_{16}$–$C_{27}$ hydrocarbon radical or a radical —CH$_2$—CHOH—CH$_2$—O—R$^6$ in which R denotes a $C_{10}$–$C_{26}$ hydrocarbon radical;

$R^5$ denotes a hydrogen atom or a mono- or polyhydroxylated $C_1$–$C_4$ hydrocarbon radical; it being possible for the said agents to be present in the form of mixtures;

(c) at least one oxidation dye.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense*, in the extracts of Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys* (Indian pipe), Aesculus sp., *Acer pseudoplatanus, Prunus persica, Pistacia palaestina*.

Among the laccases of fungal origin optionally obtained by biotechnology which can be used according to the invention, there may be mentioned the laccase(s) derived from *Polyporus versicolor, Rhizoctonia practicola* and *Rhus vernicifera* as indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae*, or variants thereof. There may also be mentioned those derived from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The lacu unit corresponds to the quantity of enzyme catalysing the conversion of 1 mmol of syringaldazine per minute at pH, 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in ulac units.

The quantities of laccase used in the compositions of the invention will vary according to the nature of the laccase chosen. Preferably, they will vary from 0.5 to 2000 ulac, or from 1000 to $4 \times 10^7$ u units, or from 20 to $2 \times 10^6$ ulac units per 100 g of composition.

The conditioning agents may be provided in liquid, semi-solid or solid form, such as for example oils, waxes or gums.

According to the invention, among the conditioning agents, the poly-α-olefins are in particular:
of the polybutene type, hydrogenated or otherwise, and preferably of the polyisobutene type, hydrogenated or otherwise.

There are preferably used the oligomers of isobutylene having a molecular weight of less than 1000 and mixtures thereof with polyisobutylenes having a molecular weight greater than 1000 and preferably of between 1000 and 15,000.

By way of examples of poly-α-olefins which can be used in the context of the present invention, there may be mentioned more particularly the products sold under the name PERMETHYL 99 A, 101 A, 102 A, 104 A (n=16) and 106 A (n=38) by the company PRESPERSE Inc, or alternatively the products sold under the name ARLAMOL HD (n=3) by the company ICI (n denoting the degree of polymerization),
of the polydecene type, hydrogenated or otherwise.

Such products are sold for example under the names ETHYLFLO by the company ETHYL CORP., and ARLAMOL PAO by the company ICI.

The fluorinated oils, fluorinated waxes and fluorinated gums are for example the perfluoropoly-ethers described in Patent Application EP-A-486135 and the fluorohydrocarbon compounds described in particular in Patent Application WO 93/11103. The teaching of these two applications is fully included in the present application by way of reference.

The term fluorohydrocarbon compounds denotes compounds whose chemical structure comprises a carbon backbone in which some hydrogen atoms have been substituted with fluorine atoms.

The perfluoropolyethers are for example sold under the trade names FOMBLIN by the company MONTEFLUOS and KRYTOX by the company DU PONT.

Among the fluorohydrocarbon compounds, there may also be mentioned the fluorinated fatty acid esters such as the product sold under the name NOFABLE FO by the company NIPPON OIL.

According to the invention, the conditioning agents may be chosen from vegetable oils such as jojoba oil, avocado oil or alternatively natural waxes such as carnauba wax or apple wax.

According to the invention, the conditioning agents may be chosen from the insoluble silicones normally used to improve the cosmetic properties of hair treated with hair formulations, namely in particular those described in Patent Applications EP-A-0181773 and EP-A-0473508.

It is of course possible to use mixtures of silicones.

Thus, according to the present invention, it is possible to use any silicone known per se, whether it is an oil, a resin or alternatively a silicone gum. The silicones are organosilicon polymers or oligomers having a branched or crosslinked, linear or cyclic structure, of variable molecular weight, which are obtained by polymerization and/or polycondensation of suitably functionalized silanes, and essentially consisting of a repetition of principal units in which the silicon atoms are linked to each other by oxygen atoms (siloxane bond), optionally substituted hydrocarbon radicals being directly linked via a carbon atom on the said silicon atoms. The most common hydrocarbon radicals are the alkyl, and in particular methyl, radicals, the fluoroalkyl radicals, the aryl, and in particular phenyl, radicals, and the alkenyl, and in particular vinyl, radicals; other types of radicals which are capable of being linked either directly, or via a hydrocarbon radical, to the siloxane chain are in particular hydrogen, halogens and in particular chlorine, bromine or fluorine, thiols, alkoxy radicals, polyoxyalkylene (or polyether), and in particular polyoxyethylene and/or polyoxypropylene, radicals, hydroxyl or hydroxyalkyl radicals, amphoteric or betaine groups, anionic groups such as carboxylates, thioglycolates, sulphosuccinates, thiosulphates, phosphates and sulphates, this list of course not being at all limiting (so-called "organomodified" silicones). In general, the silicones which can be used in the context of the present invention are those which are in particular described in "Encyclopedia of Chemical Technology, Kirk-Othmer, Third Edition, 1982, Volume 20, pp. 922 and the following pages" and in "Chemistry and Technology of Silicones, Walter NOLL, Academic Press Inc, San Diego Calif., 1968". It is also possible to use linear block copolymers comprising, in their principal chain, polysiloxane segments, such as for example polysiloxane-polyoxyalkylene or alternatively polysiloxane-polyurethane and/or polyurea block copolymers. The average molecular weight of the silicones which can be used according to the invention may vary between 100 and several millions, preferably between 1000 and 1,000,000. According to the present invention, it is of course possible to use either a single silicone, or use several different silicones.

By way of examples of silicones which can be used in the compositions according to the invention, there may be mentioned in particular polydialkyl-siloxanes, polyalkylarylsiloxanes, polydiaryldialkyl-siloxanes and more generally still all the organopolysiloxanes described in the patent application published under the number WO 93/05762 and whose teaching is, in this regard, fully included in the present application by way of reference.

According to a particularly preferred embodiment of the present invention, the silicones used are chosen from diorganopolysiloxanes (oils, gums or resins), preferably polydialkylsiloxanes or polyalkylarylsiloxanes, and still more preferably optionally modified polydimethylsiloxanes.

The silicone gums are particularly preferred and in particular those of polydialkylsiloxanes or of polyalkylarylsiloxanes. They can be used alone or as a mixture in a solvent chosen, for example, from volatile silicones, polydimethylsiloxane or polyphenylmethyl-siloxane oils, isoparaffins, pentane, dodecane or mixtures thereof.

Among the amide compounds of formula (I), there are preferred the ceramides and/or glycoceramides described by DOWNING in Arch. Dermatol, Vol. 123, 1381–1384, 1987, or those described in French Patent Application FR-2673 79, whose teachings are included here by way of reference.

The ceramides most particularly preferred according to the invention are the compounds of formula (1) for which $R^1$ denotes a saturated or unsaturated alkyl derived from $C_{16}$–$C_{22}$ fatty acids; $R^2$ denotes a hydrogen atom; and $R^3$ denotes a saturated linear $C_{15}$ radical.

Such compounds are for example:
N-linoleoyldihydrosphingosine,
N-oleoyldihydrosphingosine,
N-palmitoyldihydrosphingosine,
N-stearoyldihydrosphingosine,
N-behenoyldihydrosphingosine,
or the mixtures of these compounds.

It is also possible to use the compounds of formula (1) for which $R^1$ denotes a saturated or unsaturated alkyl radical derived from fatty acids; $R^2$ denotes a galactosyl or sulphogalactosyl radical; and $R^3$ denotes a group —CH═CH—(CH$_2$)$_{12}$—CH$_3$.

By way of example, there may be mentioned the product consisting of a mixture of glycoceramides, sold under the trade name GLYCOCER by the company WAITAKI INTERNATIONAL BIOSCIENCES.

It is also possible to use the compounds of formula (1) described in Patent Applications EP-A-0227994 and WO94/07844.

Such compounds are for example QUESTAMIDE H (bis(N-hydroxyethyl-N-cetyl)malonamide) sold by the company QUEST, N-(2-hydroxyethyl)-N-(3-Cetyloxy-2-hydroxypropyl)amide of cetylic acid.

It is possible to use the N-docasanoyl-N-methyl-D-glucamine described in Patent Application WO92/05764.

In the present invention, it is preferable to use, as conditioning agent insoluble in aqueous media, natural waxes, vegetable oils, insoluble silicones and fatty amides as described above.

The conditioning agent(s) are present in the compositions in accordance with the invention in proportions generally of between 0.001 and 10% by weight, preferably from 0.01 to 5% by weight, and still more particularly from 0.1 to 2% by weight relative to the total weight of the composition.

The nature of the oxidation dye(s) used in the ready-to-use dyeing composition is not critical. They are chosen from oxidation bases and/or couplers.

The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (I) and their addition salts with an acid:

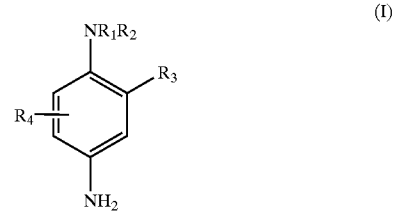

in which:
$R_1$ represents a hydrogen atom, a $C_1$–$C_4$ alkyl radical, a monohydroxy($C_1$–$C_4$ alkyl) radical, a polyhydroxy-($C_2$-C4 alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_2$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–C4 alkoxy) radical, a mesylamino($C_1$–$C_4$ alkoxy) radical or a carbamoylamino($C_1$–$C_4$ alkoxy) radical, $R_4$ represents a hydrogen or halogen atom or a $C_1$–$C_4$ alkyl radical.

Among the nitrogen-containing groups of formula (I) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly paraphenylenediamine, para-tolylenediamine, 2-Chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

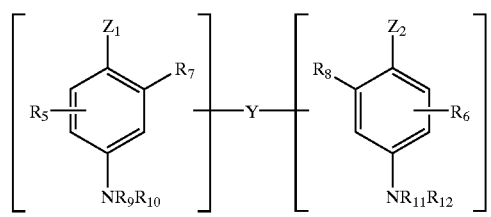

(II)

in which:

Z$_1$ and Z$_2$, which are identical or different, represent a hydroxyl or —NH$_2$ radical which may be substituted with a C$_1$–C$_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or C$_1$–C$_6$ alkoxy radicals;

R$_5$ and R$_6$ represent a hydrogen or halogen atom, a C$_1$–C$_4$ alkyl radical, a monohydroxy(C$_1$–C$_4$ alkyl) radical, a polyhydroxy(C$_2$–C$_4$ alkyl) radical, an amino(C$_1$–C$_4$ alkyl) radical or a linking arm Y;

R$_7$, R$_8$, R$_9$, R$_{10}$, R$_{11}$ and R$_{12}$, which are identical or different, represent a hydrogen atom, a linking arm Y or a C$_1$–C$_4$ alkyl radical;

it being understood that the compounds of formula (II) contain only one linking arm Y per molecule.

Among the nitrogen-containing groups of formula (II) above, there may be mentioned in particular the amino, mono(C$_1$–C$_4$)alkylamino, (C$_1$–C$_4$) dialkylamino, (C$_1$–C$_4$) trialkylamino, monohydroxy(C$_1$–C$_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis (2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (III), and their addition salts with an acid:

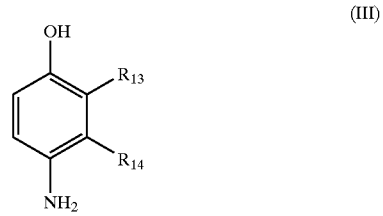

(III)

in which:

R$_{13}$ represents a hydrogen or halogen atom, a C$_1$–C$_4$ alkyl, monohydroxy (C$_1$–C4 alkyl), (C$_1$–C$_4$) alkoxy (C$_1$–C$_4$)-alkyl, amino(C$_1$–C$_4$ alkyl) or hydroxy(C$_1$–C$_4$) alkylamino-(C$_1$–C$_4$ alkyl) radical, R$_{14}$ represents a hydrogen or halogen atom, a C$_1$–C4 alkyl, monohydroxy (C$_1$–C4 alkyl), polyhydroxy (C$_2$–C$_4$ alkyl), amino(C$_1$–C$_4$ alkyl), cyano(C$_1$–C$_4$ alkyl) or (C$_1$–C4)alkoxy(C$_1$–C$_4$)alkyl radical, it being understood that at least one of the radicals R$_{13}$ or R$_{14}$ represents a hydrogen atom.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylamino-pyrazole, 3,5-diamino-4-(β-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (IV), their addition salts with an acid or with a base and their tautomeric forms, when a tautomeric equilibrium exists:

$$(\text{X})_i \text{---} \underset{(\text{OH})_n}{\overset{\text{N}}{\underset{\text{N-N}}{\bigcirc}}} \text{---} [\text{NR}_{15}\text{R}_{16}]_p \quad [\text{NR}_{17}\text{R}_{18}]_q \quad (\text{IV})$$

in which:

$R_{15}$, $R_{16}$, $R_{17}$ and $R_{18}$, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $(C_1$–$C_4)$alkoxy$(C_1$–$C_4$ alkyl) radical, a $C_1$–$C_4$ aminoalkyl radical (it being possible for the amine to be protected with an acetyl, ureido or sulphonyl radical), a $(C_1$–$C_4)$ alkylamino$(C_1$–$C_4$ alkyl) radical, a di-[$(C_1$–$C_4)$alkyl]amino$(C_1$–$C_4$ alkyl) radical (it being possible for the dialkyl radicals to form a carbon-containing ring or a 5- or 6-membered heterocycle), a hydroxy$(C_1$–$C_4)$alkyl- or di-[hydroxy$(C_1$–$C_4)$alkyl]-amino$(C_1$–$C_4$ alkyl) radical, the X radicals, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a $(C_1$–$C_4)$ alkylamino$(C_1$–$C_4$ alkyl) radical, a di-[$(C_1$–$C_4)$alkyl]amino$(C_1$–$C_4$ alkyl) radical (it being possible for the dialkyls to form a carbon-containing ring or a 5- or 6-membered heterocycle), a hydroxy$(C_1$–$C_4)$alkyl or di-[hydroxy$(C_1$–$C_4)$alkyl]-amino$(C_1$–$C_4$ alkyl) radical, an amino radical, a $(C_1$–$C_4)$alkyl- or di-[$(C_1$–$C_4)$alkyl]-amino radical; a halogen atom, a carboxylic acid group, a sulphonic acid group;

i equals 0, 1, 2 or 3;

p equals 0 or 1;

q equals 0 or 1;

n equals 0 or 1;

with the proviso that:

the sum p+q is different from 0;

when p+q is equal to 2, then n equals 0 and the groups $NR_{15}R_{16}$ and $NR_{17}R_{18}$ occupy positions (2,3); (5,6); (6,7); (3,5) or (3,7);

when p+q is equal to 1, then n equals 1 and the group $NR_{15}R_{16}$ (or $NR_{17}R_{18}$) and the OH group occupy positions (2,3); (5,6); (6,7); (3,5) or (3,7).

When the pyrazolo[1,5-a]pyrimidines of formula (IV) above are such that they comprise a hydroxyl group on one of the positions 2, 5 or 7 at the α position with respect to a nitrogen atom, a tautomeric equilibrium exists which is represented for example by the following scheme:

$$\underset{\text{OH}}{\overset{\text{N}}{\underset{\text{N-N}}{\bigcirc}}}\text{--NR}_{15}\text{R}_{16} \quad \rightleftharpoons \quad \underset{\text{O}}{\overset{\text{H, N}}{\underset{\text{N-N}}{\bigcirc}}}\text{--NR}_{15}\text{R}_{16}$$

Among the pyrazolo[1,5-a]pyrimidines of formula (IV) above, there may be mentioned in particular:

pyrazolo[1,5-a]pyrimidine-3,7-diamine;

2,5-dimethylpyrazolo[1,5-a]pyrimidine-3,7-diamine;

pyrazolo[1,5-a]pyrimidine-3,5-diamine;

2,7-dimethylpyrazolo[1,5-a]pyrimidine-3,5-diamine;

3-aminopyrazolo[1,5-a]pyrimidin-7-ol;

3-aminopyrazolo[1,5-a]pyrimidin-5-ol;

2-(3-aminopyrazolo[1,5-a]pyrimidin-7-ylamino)ethanol;

2-(7-aminopyrazolo[1,5-a]pyrimidin-3-ylamino)ethanol;

2-[(3-aminopyrazolo[1,5-a]pyrimidin-7-yl)(2-hydroxy-ethyl) amino] ethanol;

2-[(7-aminopyrazolo[1,5-a]pyrimidin-3-yl)(2-hydroxy-ethyl)amino]ethanol;

5,6-dimethylpyrazolo[1,5-a]pyrimidine-3,7-diamine;

2,6-dimethylpyrazolo[1,5-a]pyrimidine-3,7-diamine;

2,5,N7,N7-tetramethylpyrazolo[1,5-a]pyrimidine-3,7-diamine;

and their addition salts and their tautomeric forms, when a tautomeric equilibrium exists.

The pyrazolo[1,5-a]pyrimidines of formula (IV) above may be prepared by cyclization from an aminopyrazole according to the syntheses described in the following references:

EP 628559 BEIERSDORF-LILLY

R. Vishdu, H. Navedul, Indian J. Chem., 34b(6), 514, 1995.

N. S. Ibrahim, K. U. Sadek, F. A. Abdel-Al, Arch. Pharm., 320, 240, 1987.

R. H. Springer, M. B. Scholten, D. E. O'Brien, T. Novinson, J. P. Miller, R. K. Robins, J. Med. Chem., 25, 235, 1982.

T. Novinson, R. K. Robins, T. R. Matthews, J. Med. Chem., 20, 296, 1977.

U.S. Pat. No. 3,907,799 ICN PHARMACEUTICALS

The pyrazolo[1,5-a]pyrimidines of formula (IV) above can also be prepared by cyclization from ydrazine according to the syntheses described in the following references:

A. McKillop and R. J. Kobilecki, Heterocycles, 6(9), 1355, 1977.

E. Alcade, J. De Mendoza, J. M. Marcia-Marquina, C. Almera, J. Elguero, J. Heterocyclic Chem., 11(3), 423, 1974.

K. Saito, I. Hori, M. Higarashi, H. Midorikawa, Bull. Chem. Soc. Japan, 47(2), 476, 1974.

The oxidation base(s) preferably represent from 0.0005 to 12% by weight approximately of the total weight of the dyeing composition in accordance with the invention, and still more preferably from 0.005 to 6% by weight approximately of this weight.

The coupler(s) which can be used in the ready-to-use dyeing composition in accordance with the invention are those conventionally used in oxidation dyeing compositions, that is to say meta-phenylene-diamines, meta-aminophenols, meta-diphenols, heterocyclic couplers, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2–C]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

In general, the addition salts with an acid of the oxidation dyes which can be used in the context of the dyeing compositions of the invention (oxidation bases and couplers) are in particular chosen from hydrochlorides, hydrobromides, sulphates and tartrates, lactates and acetates.

The dyeing composition of the invention may also contain, in addition to the oxidation dyes defined above, direct dyes in order to increase the shimmer of the shades. These direct dyes may in particular then be chosen from nitro, azo or anthraquinone dyes.

The ready-to-use dyeing composition in accordance with the invention may also contain various adjuvants conventionally used in hair dyeing compositions, such as anionic, cationic, nonionic, amphoteric or zwitterionic surfactants or mixtures thereof, polymers, thickeners, antioxidants, enzymes different from the laccases used in accordance with the invention, such as for example peroxidases or oxidoreductases containing 2 electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the ready-to-use dyeing composition in accordance with the invention are not, or substantially not, impaired by the addition(s) envisaged.

The ready-to-use dyeing composition in accordance with the invention can be provided in various forms, such as in the form of liquids, creams, gels, optionally pressurized, or in any other form appropriate for dyeing keratinous fibres, in particular human hair. In this case, the oxidation dye(s) and the laccase(s) are present in the same ready-to-use composition, and consequently the said composition should be free of gaseous oxygen, so as to avoid any premature oxidation of the oxidation dye(s).

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye as defined above and, on the other hand, a composition (B) containing, in a medium appropriate for dyeing, at least one enzyme of the laccase type and at least one conditioning agent insoluble in aqueous media as defined above, and then in mixing them at the time of use before applying this mixture to the keratinous fibres.

According to a particular embodiment of the invention, the insoluble conditioning agent may be incorporated into the composition (A).

Another subject of the invention is a multi-compartment device or dyeing (kit) or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The medium appropriate for keratinous fibres (or carrier) of the ready-to-use dyeing compositions for keratinous fibres in accordance with the invention generally consists of water or of a mixture of water and of at least one organic solvent in order to solubilize the compounds which might not be sufficiently soluble in water. As organic solvent, there may be mentioned for example $C_1$–$C_4$ alkanols such as ethanol and isopropanol as well as aromatic alcohols such as benzyl alcohol, similar products and mixtures thereof.

The solvents may be present in proportions preferably of between 1 and 40% by weight approximately relative to the total weight of the dyeing composition, and still more preferably between 5 and 30% by weight approximately.

The pH of the ready-to-use dyeing compositions for keratinous fibres in accordance with the invention is chosen such that the enzymatic activity of the laccase is not impaired. It generally varies from 4 to 11 approximately, and more preferably from 6 to 9 approximately.

Concrete examples illustrating the invention will now be given.

In the text which follows and in the preceding text, unless otherwise stated, the percentages are expressed by weight. The following examples illustrate the invention with no limitation being implied.

EXAMPLE

Dyeing Composition

The following ready-to-use dyeing composition was prepared (contents in grams):

Laccase obtained from Rhus vernicifera 1.8 g containing 180 units/mg marketed by the company SIGMA ($C_8$–$C_{10}$)Alkyl polyglucoside in aqueous 16.5 g solution containing 60% of active substance (AS) sold under the name ORAMIX CG110 by the company SEPPIC Paraphenylenediamine 0.254 g 2,4-Diaminophenoxyethanol dihydrochloride 0.260 g.

Dimethicone sold under the name MIRASIL 0.5 g DM 500,000 by the company RHONE POULENC Ethanol 20.0 g pH agent qs pH 6.5

Demineralized water qs 100 g

This ready-to-use dyeing composition is applied to locks of natural grey hair which is 90% white for 40 minutes at 30° C. The hair is then rinsed, washed with a standard shampoo and then dried.

Locks of hair with bluish grey colour are obtained.

In this example, 1.8 g of laccase obtained from Rhus vernicifera containing 180 units/mg can be replaced with 1 g of laccase obtained from Pyricularia Orizae containing 100 units/mg sold by the company I.C.N.

What is claimed is:

1. A composition for the oxidation dyeing of keratinous fibers, comprising:

(a) at least one enzyme of the laccase type;

(b) at least one conditioning agent insoluble in aqueous media, chosen from poly-α-olefins, fluorinated oils, vegetable oils, natural waxes, fluorinated waxes, fluorinated gums, fatty acid esters chosen from ethyl and isopropyl palmitates, 2-ethylhexyl palmitate, 2-octyidecyl palmitate, butyl, cetyl and 2-octyidodecyl myristates, hexyl stearate, butyl stearate, dioctyl maleate, hexyl laurate, 2-hexyldecyl laurate and isononyl isononanate, silicones, and amide compounds comprising at least one fatty chain chosen from those of the formula (1):

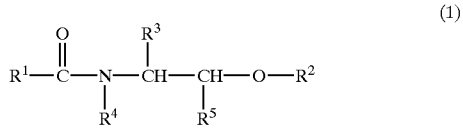

in which:

$R^1$ is chosen from saturated and unsaturated, linear and branched, $C_9$–$C_{30}$ hydrocarbon groups, it being possible for these groups to be substituted with at least one substituent chosen from hydroxyl groups optionally esterified with an acid chosen from saturated and unsaturated $C_{16}$–$C_{30}$ fatty acids, and R''—(NR—CO)$_n$—R'— groups in which n is equal to 0 or 1, R is chosen from a hydrogen atom and hydroxyethyl groups, R' and R'' are identical or different and are each chosen from hydrocarbon groups, optionally substituted, in which the sum of the carbon atoms varies from 9 to 30, R' being a divalent group;

$R^2$ is chosen from a hydrogen atom, (glycosyl)$_n$ groups, (galactosyl)$_m$ groups and sulphogalactosyl groups in which n is an integer varying from 1 to 4 and m is an integer varying from 1 to 8;

$R^3$ is chosen from a hydrogen atom, saturated and unsaturated $C_{15}$–$C_{27}$ hydrocarbon groups, it being possible for these groups to be substituted with at least one $C_1$–$C_{14}$ alkyl group; $R^3$ may also be chosen from $C_{15}$–$C_{26}$ α-hydroxyalkyl groups, wherein the hydroxyl group of said α-hydroxyalkyl group is optionally esterified with an acid chosen from $C_{16}$–$C_{30}$ α-hydroxy acids;

$R^4$ is chosen from a hydrogen atom, saturated and unsaturated $C_{16}$–$C_{27}$ hydrocarbon groups, optionally substituted, and —CH$_2$—CHOH—CH$_2$—O—R$^6$ groups in which $R^6$ is chosen from $C_{10}$–$C_{26}$ hydrocarbon groups, optionally substituted;

$R^5$ is chosen from a hydrogen atom and mono- and polyhydroxylated $C_1$–$C_4$ hydrocarbon groups; and (c) at least one oxidation dye.

2. A composition according to claim 1, wherein said keratinous fibers are human keratinous fibers.

3. A composition according to claim 2, wherein said human keratinous fibers are hair.

4. A composition according to claim 1, wherein said at least one enzyme of the laccase type is chosen from laccases of plant origin, animal origin, fungal origin, and bacterial origin, and laccases obtained by biotechnology.

5. A composition according to claim 1, wherein said at least one enzyme of the laccase type is chosen from those produced by plants performing chlorophyll synthesis.

6. A composition according to claim 1, wherein said at least one enzyme of the laccase type is chosen from those extracted from plants chosen from Anacardiaceae, Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys*, Aesculus sp., *Acer pseudoplatanus, Prunus persica*, and *Pistacia palaestina*.

7. A composition according to claim 1, wherein said at least one enzyme of the laccase type is chosen from those derived from fungi chosen from *Pyricularia orizae, Polyporus versicolor, Rhizoctonia praticola, Rhus vernicifera*, Scytalidium, *Polyporus pinsitus, Myceliophtora thermophila, Rhizoctonia solani, Tramates versicolor, Fomes fomentarius, Chaetomium thermophile, Neurospora crassa, Coriolus versicol, Botrytis cinerea, Rigidoporus*

*lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all of said fungi.

8. A composition according to claim 1, wherein said at least one enzyme of the laccase type is in a quantity ranging from 0.5 to 2000 lacu units per 100 g of said composition.

9. A composition according to claim 1, wherein said at least one enzyme of the laccase type is in a quantity ranging from 1000 to $4 \times 10^7$ u units per 100 g of said composition.

10. A composition according to claim 1, wherein said at least one enzyme of the laccase type is in a quantity ranging from 20 to $2 \times 10^6$ lacu units per 100 g of said composition.

11. A composition according to claim 1, wherein said at least one conditioning agent is in liquid, semisolid or solid form.

12. A composition according to claim 11, wherein said at least one conditioning agent is in the form of an oil, wax or gum.

13. A composition according to claim 1, wherein said at least one conditioning agent is chosen from vegetable oils, natural waxes, silicones and the amide compounds of formula (1).

14. A composition according to claim 1, wherein said poly-α-olefins are chosen from
 polybutene type groups, optionally hydrogenated, and
 polydecene type groups, optionally hydrogenated.

15. A composition according to claim 14, wherein said polybutene type groups are polyisobutene type groups, optionally hydrogenated.

16. A composition according to claim 1, wherein said silicones are chosen from polydialkylsiloxanes, polyalkylarylsiloxanes, and polydiaryldialkylsiloxanes, optionally substituted.

17. A composition according to claim 1, wherein said silicones are chosen from polydialkylsiloxanes and polyalkylarylsiloxanes, optionally substituted.

18. A composition according to claim 1, wherein said silicones are polydimethylsiloxanes, optionally substituted.

19. A composition according to claim 1, wherein said silicones are chosen from polydialkylsiloxane gums and polyalkylarylsiloxane gums.

20. A composition according to claim 1, wherein in formula (1) of the amide compounds, $R^1$ is chosen from saturated and unsaturated alkyl groups derived from $C_{16}$–$C_{22}$ fatty acids; $R^2$ is a hydrogen atom; and $R^3$ is a saturated linear $C_{15}$ group.

21. A composition according to claim 1, wherein said amide compounds are chosen from:
 N-linoleoyldihydrosphingosine,
 N-oleoyldihydrosphingosine,
 N-palmitoydihydrosphingosine,
 N-stearoyldihydrosphingosine,and
 N-behenoyidihydrosphingosine.

22. A composition according to claim 1, wherein in formula (1) of said amide compounds, $R^1$ is chosen from saturated and unsaturated alkyl groups derived from fatty acids; $R^2$ is chosen from galactosyl groups and sulphogalactosyl groups; and $R^3$ is the group —CH=CH—$(CH_2)_{12}$—$CH_3$.

23. A composition according to claim 1, wherein said at least one conditioning agent is present in a concentration ranging from 0.001% to 10% by weight relative to the total weight of the composition.

24. A composition according to claim 23, wherein said at least one conditioning agent is present in a concentration ranging from 0.01% to 5% by weight relative to the total weight of the composition.

25. A composition according to claim 24, wherein said at least one conditioning agent is present in a concentration ranging from 0.1% to 2% by weight relative to the total weight of the composition.

26. A composition according to claim 1, wherein said at least one oxidation dye is at least one oxidation base chosen from ortho- and para-phenylenediamines, bisphenylalkylenediamines, ortho- and para-aminophenols, heterocyclic bases, and the acid addition salts of all of said at least one oxidation bases.

27. A composition according to claim 26, wherein said at least one oxidation base is present in a concentration ranging from 0.0005% to 12% by weight relative to the total weight of the composition.

28. A composition according to claim 1, wherein said at least one oxidation dye is at least one coupler chosen from meta-phenylenediamines, meta-aminophenols, meta-diphenols, heterocyclic couplers, and the acid addition salts of all of said at least one couplers.

29. A composition according to claim 28, wherein said at least one coupler is present in a concentration ranging from 0.0001% to 10% by weight relative to the total weight of the composition.

30. A composition according to claim 26, wherein said acid addition salts are chosen from hydrochlorides, hydrobromides, sulphates, tartrates, lactates and acetates.

31. A composition according to claim 28, wherein said acid addition salts are chosen from hydrochlorides, hydrobromides, sulphates, tartrates, lactates and acetates.

32. A composition according to claim 1, further comprising at least one direct dye.

33. A composition according to claim 1, further comprising at least one carrier appropriate for keratinous fibers.

34. A composition according to claim 33, wherein said at least one carrier comprises a substance chosen from water and at least one organic solvent.

35. A composition according to claim 34, wherein said at least one organic solvent is present in a concentration ranging from 1% to 40% by weight relative to the total weight of the composition.

36. A composition according to claim 35, wherein said at least one organic solvent is present in a concentration ranging from 5% to 30% by weight relative to the total weight of the composition.

37. A composition according to claim 1, wherein the pH varies from about 4 to about 11.

38. A composition according to claim 37, wherein the pH varies from about 6 to about 9.

39. A composition according to claim 1, further comprising at least one suitable cosmetic adjuvant chosen from surfactants, polymers, thickening agents, anitoxids, enzymes different from said at least one enzyme of the laccase type as defined in claim 1, penetrating agents, sequestering agents, perfumes, buffers, dispersing agents, film-forming agents, screening agents, vitamins, preservatives and opacifying agents.

40. A method of dyeing keratinous fibers, comprising applying to said keratinous fibers for a sufficient time to develop a desired color at least one dyeing composition comprising:

(a) at least one enzyme of the laccase type;
(b) at least one conditioning agent insoluble in aqueous media, chosen from poly-α-olefins, fluorinated oils, vegetable oils, natural waxes, fluorinated waxes, fluorinated gums, fatty acid esters chosen from ethyl and isopropyl palmitates, 2-ethylhexyl palmitate, 2-octyldecyl palmitate, butyl, cetyl and 2-octyldodecyl myristates, hexyl stearate, butyl stearate, dioctyl maleate, hexyl laurate, 2-hexyldecyl laurate and isononyl isononanate, silicones, and amide compounds comprising at least one fatty chain chosen from those of the formula (1):

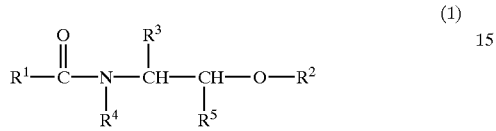

(1)

in which:
$R^1$ is chosen from saturated and unsaturated, linear and branched, $C_9$–$C_{30}$ hydrocarbon groups, it being possible for these groups to be substituted with at least one substituent chosen from hydroxyl groups optionally esterified with an acid chosen from saturated and unsaturated $C_{16}$–$C_{30}$ fatty acids, and R"—(NR—CO)$_n$—R'— groups in which n is equal to 0 or 1, R is chosen from a hydrogen atom and hydroxyethyl groups, R' and R" are identical or different and are each chosen from hydrocarbon groups, optionally substituted, in which the sum of the carbon atoms varies from 9 to 30, R' being a divalent group;
$R^2$ is chosen from a hydrogen atom, (glycosyl)$_n$ groups, (galactosyl)$_m$ groups and sulphogalactosyl groups in which n is an integer varying from 1 to 4 and m is an integer varying from 1 to 8;
$R^3$ is chosen from a hydrogen atom, saturated and unsaturated $C_{15}$–$C_{27}$ hydrocarbon groups, it being possible for these groups to be substituted with at least one $C_1$–$C_{14}$ alkyl group; $R^3$ may also be chosen from $C_{15}$–$C_{26}$ α-hydroxyalkyl groups, wherein the hydroxyl group of said α-hydroxyalkyl group is optionally esterified with an acid chosen from $C_{16}$–$C_{30}$ α-hydroxy acids;
$R^4$ is chosen from a hydrogen atom, saturated and unsaturated $C_{16}$–$C_{27}$ hydrocarbon groups, optionally substituted, and —CH$_2$—CHOH—CH$_2$—O—R$^6$ groups in which $R^6$ is chosen from $C_{10}$–$C_{26}$ hydrocarbon groups, optionally substituted;
$R^5$ is chosen from a hydrogen atom and mono- and polyhydroxylated $C_1$–$C_4$ hydrocarbon groups; and
(c) at least one oxidation dye.

41. A method of dyeing keratinous fibers according to claim 40, wherein said keratinous fibers are human keratinous fibers.

42. A method of dyeing keratinous fibers according to claim 41, wherein said human keratinous fibers are hair.

43. A method of dyeing keratinous fibers, comprising the steps of
(a) storing a first composition,
(b) storing a second composition separately from said first composition,
(c) mixing the first composition with the second composition to form a mixture, and
(d) applying said mixture to said keratinous fibers for a time sufficient to achieve a desired coloration, wherein said first composition comprises, in a medium appropriate for dyeing, at least one oxidation dye,
wherein said second composition comprises, in a medium appropriate for keratinous fibers, at least one enzyme of the laccase type, and
further wherein at least one of said first composition and said second composition comprises at least one conditioning agent insoluble in aqueous media, chosen from poly-α-olefins, fluorinated oils, vegetable oils, natural waxes, fluorinated waxes, fluorinated gums, fatty acid esters chosen from ethyl and isopropyl palmitates, 2-ethylhexyl palmitate, 2-octyidecyl palmitate, butyl, cetyl and 2-octyldodecyl myristates, hexyl stearate, butyl stearate, dioctyl maleate, hexyl laurate, 2-hexyldecyl laurate and isononyl isononanate, silicones, and amide compounds comprising at least one fatty chain chosen from those of the formula (1):

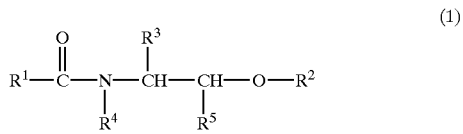

(1)

in which:
$R^1$ is chosen from saturated and unsaturated, linear and branched, $C_9$–$C_{30}$ hydrocarbon groups, it being possible for these groups to be substituted with at least one substituent chosen from hydroxyl groups optionally esterified with an acid chosen from saturated and unsaturated $C_{16}$–$C_{30}$ fatty acids, and R"—(NR—CO)$_n$—R'— groups in which n is equal to 0 or 1, R is chosen from a hydrogen atom and hydroxyethyl groups, R' and R" are identical or different and are each chosen from hydrocarbon groups, optionally substituted, in which the sum of the carbon atoms varies from 9 to 30, R' being a divalent group;
$R^2$ is chosen from a hydrogen atom, (glycosyl)$_n$ groups, (galactosyl)$_m$ groups and sulphogalactosyl groups in which n is an integer varying from 1 to 4 and m is an integer varying from 1 to 8;
$R^3$ is chosen from a hydrogen atom, saturated and unsaturated $C_{15}$–$C_{27}$ hydrocarbon groups, it being possible for these groups to be substituted with at least one $C_1$–$C_{14}$ alkyl group; $R^3$ may also be chosen from $C_{15}$–$C_{26}$ α-hydroxyalkyl groups, wherein the hydroxyl group of said α-hydroxyalkyl group is optionally esterified with an acid chosen from $C_{16}$–$C_{30}$ α-hydroxy acids;
$R^4$ is chosen from a hydrogen atom, saturated and unsaturated $C_{16}$–$C_{27}$ hydrocarbon groups, optionally substituted, and
—CH$_2$—CHOH—CH$_2$—O—R$^6$ groups in which $R^6$ is chosen from $C_{10}$–$C_{26}$ hydrocarbon groups, optionally substituted;
$R^5$ is chosen from a hydrogen atom and mono- and polyhydroxylated $C_1$–$C_4$ hydrocarbon groups.

44. A multicompartment device or a dyeing kit, comprising a first compartment containing a composition (A) comprising, in a medium appropriate for dyeing, at least one oxidation dye and a second compartment containing a composition (B) comprising, in a medium appropriate for keratinous fibers, at least one enzyme of the laccase type, wherein at least one of said composition (A) and composition (B) comprises at least one conditioning agent insoluble in aqueous media, chosen from poly-α-olefins, fluorinated oils, vegetable oils, natural waxes, fluorinated waxes, fluorinated gums, fatty acid esters chosen from ethyl and isopropyl palmitates, 2-ethylhexyl palmitate, 2-octyldecyl palmitate, butyl, cetyl and 2-octyldodecyl myristates, hexyl stearate, butyl stearate, dioctyl maleate, hexyl laurate, 2-hexyldecyl laurate and isononyl isononanate, silicones, and amide compounds comprising at least one fatty chain chosen from those of the formula (1):

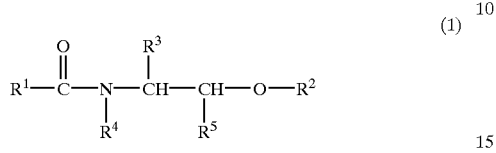

(1)

in which:

$R^1$ is chosen from saturated and unsaturated, linear and branched, $C_9$–$C_{30}$ hydrocarbon groups, it being possible for these groups to be substituted with at least one substituent chosen from hydroxyl groups optionally esterified with an acid chosen from saturated and unsaturated $C_{16}$–$C_{30}$ fatty acids, and R"—(NR—CO)$_n$—R'— groups in which n is equal to 0 or 1, R is chosen from a hydrogen atom and hydroxyethyl groups, R' and R" are identical or different and are each chosen from hydrocarbon groups, optionally substituted, in which the sum of the carbon atoms varies from 9 to 30, R' being a divalent group;

$R^2$ is chosen from a hydrogen atom, (glycosyl)$_n$ groups, (galactosyl)$_m$ groups and sulphogalactosyl groups in which n is an integer varying from 1 to 4 and m is an integer varying from 1 to 8;

$R^3$ is chosen from a hydrogen atom, saturated and unsaturated $C_{15}$–$C_{27}$ hydrocarbon groups, it being possible for these groups to be substituted with at least one $C_1$–$C_{14}$ alkyl group; $R^3$ may also be chosen from $C_{15}$–$C_{26}$ α-hydroxyalkyl groups, wherein the hydroxyl group of said α-hydroxyalkyl group is optionally esterified with an acid chosen from $C_{16}$–$C_{30}$ α-hydroxy acids;

$R^4$ is chosen from a hydrogen atom, saturated and unsaturated $C_{16}$–$C_{27}$ hydrocarbon groups, optionally substituted, and —$CH_2$—CHOH—$CH_2$—O—$R^6$ groups in which $R^6$ is chosen from $C_{10}$–$C_{26}$ hydrocarbon groups, optionally substituted;

$R^5$ is chosen from a hydrogen atom and mono and polyhydroxylated $C_1$–$C_4$ hydrocarbon groups.

* * * * *

UNITED STATES PATENT AND TRADEMARK OFFICE
CERTIFICATE OF CORRECTION

PATENT NO.    : 6,626,962 B1
DATED         : September 30, 2003
INVENTOR(S)   : Gérard Lang and Jean Cotteret It is certified that error appears in the above-identified patent and that said Letters Patent is hereby corrected as shown below:

<u>Column 13,</u>
Line 62, "2-octyidecyl" should read -- 2-octyldecyl --.
Line 62, "2-octyidodecyl" should read -- 2-octyldodecyl --.

<u>Column 15,</u>
Lines 45-46, "andpolyalkylarylsiloxane" should read -- and polyalkylarylsiloxane --.
Line 57, "N-palmitoydihydrosphingosine," should read
-- N-palmitoyldihydrosphingosine, --.
Line 58, "N-stearoyldihydrosphingosine,and" should read
-- N-stearoyldihydrosphingosine, and --.
Line 59, N-behenoyidihydrosphingosine." should read
-- N-behenoyldihydrosphingosine. --.

<u>Column 18,</u>
Line 13, "2-octyidecyl" should read -- 2-octyldecyl --.

<u>Column 20,</u>
Line 24, "mono" should read -- mono- --.

Signed and Sealed this

Twenty-seventh Day of January, 2004

JON W. DUDAS
*Acting Director of the United States Patent and Trademark Office*